(12) United States Patent  
Mahler

(10) Patent No.: US 6,406,295 B1  
(45) Date of Patent: Jun. 18, 2002

(54) IDENTIFICATION OF DENTAL IMPLANT COMPONENTS

(76) Inventor: Brian A. Mahler, 3005 Oakton Meadows, Oakton, VA (US) 22124

( * ) Notice: Subject to any disclaimer, the term of this patent is extended or adjusted under 35 U.S.C. 154(b) by 0 days.

(21) Appl. No.: 09/903,499

(22) Filed: Jul. 13, 2001

(51) Int. Cl.[7] .................................................. A61C 8/00
(52) U.S. Cl. ..................................................... 433/173
(58) Field of Search ................................ 433/172, 173, 433/174, 175, 176

(56) References Cited

U.S. PATENT DOCUMENTS

| | | | |
|---|---|---|---|
| 5,104,322 A | | 4/1992 | You ........................... 433/224 |
| 5,289,919 A | | 3/1994 | Fischer ........................ 433/77 |
| 5,350,301 A | * | 9/1994 | De Buck ..................... 433/173 |
| 5,525,314 A | * | 6/1996 | Hurson ........................ 206/369 |
| 5,919,042 A | | 7/1999 | Williams ...................... 433/19 |
| 5,941,706 A | | 8/1999 | Ura ............................. 433/165 |
| 6,227,856 B1 | * | 5/2001 | Beaty et al. ................. 433/172 |
| 6,305,939 B1 | * | 10/2001 | Dawood ...................... 433/174 |

\* cited by examiner

Primary Examiner—Cary E. O'Connor  
(74) Attorney, Agent, or Firm—Andrew M. Hill

(57) ABSTRACT

A method of identifying healing caps and impression copings of a system of implant components used in a dental implantation procedure utilizing a permanent implanted base, wherein healing caps and impression copings are distinguished according to structural characteristics. The healing caps are classified according to width or diameter taken at the lower surface which abuts the implant, for compatibility with width or diameter of the restorative platform, height, and maximum diameter. Impression copings are classified according to width or diameter taken at the lower surface, and according to maximum diameter. Widths or diameters taken at the lower surface are preferably indicated by color coding. Other characteristics are indicated by indicia such as alphanumeric characters. Where alphanumeric characters are utilized, alphabetic characters denote one characteristic and numeric characters denote a second characteristic consistently between both healing caps and impression copings. Color coding and indicia may be replaced by surface texturing and other visually perceptible characteristics.

16 Claims, 4 Drawing Sheets

IDENTIFICATION OF DENTAL IMPLANT COMPONENTS

BACKGROUND OF THE INVENTION

1. Field of the Invention

The present invention relates to dental implants, and more particularly to establishing identity of implants and associated peripheral components, for the purpose of assuring that compatible components are utilized in dental procedures as peripheral components are installed and subsequently replaced with others.

2. Description of the Prior Art

The field of dental implants has grown greatly in recent years. As part of this trend, the number of components of an implant has increased. Implants, healing caps, impression copings, and restorative abutments are all utilized at various stages of the implant procedure. An implant may vary in diameter and also in the nature of mechanical connection to its associated components, as well as in other ways. Each one of these variations requires corresponding variation in structure of its associated components. Healing caps and impression copings may vary in height, width, and contour. It becomes apparent then, that the total number of different components of an uncomplicated system of dental components rises in the scores.

It is not an easy matter to distinguish among the many variations of components. This becomes necessary when it comes time to remove a component and install a different type of component as the implant procedure progresses. Difficulties in successful identification arise firstly, from the size of the components. Overall length of these components may be on the order of three eights of an inch (nine mm), and visual identification is not readily accomplished. For example, identifying a healing cap or abutment which is 5.0 mm in diameter from an abutment 6.0 mm in diameter may possibly not be accomplished without having a reference abutment at hand for ready comparison. Another problem is that a dental practitioner may not practice implant procedures frequently. This results in reduced familiarity with implant components by both the practitioner and his or her support personnel who may be tasked with cleaning, sterilizing, sorting, and dispensing implant components.

There exists a need in the implant art for rendering the many varieties of implant components readily recognizable primarily by visual inspection. Color has been utilized for this purpose in the dental arts. Examples are seen in U.S. Pat. No. 5,104,322, issued to Moo C. You on Apr. 14, 1992, U.S. Pat. No. 5,289,919, issued to Dan E. Fischer on Mar. 1, 1994, U.S. Pat. No. 5,919,042, issued to Michael O. Williams on Jul. 6, 1999, and U.S. Pat. No. 5,941,706, issued to Robert S. Ura on Aug. 24, 1999. You utilizes color to differentiate among different root canal sealers. Fischer utilizes color to differentiate among different delivery tips for syringes. Williams provides graduation marks in an orthodontic expanding and positioning appliance to indicate adjusted length thereof. Ura sets forth root canal cleaners and sealers which utilize color coding to indicate size thereof. None of these schemes relates to identifying associated members of families of implant components, as seen in the present invention.

Current practice in the field of implants has utilized color for identifying associated implant components, but only to a limited degree which does not solve the problem of recognizing appropriate components of an implant throughout the term of the procedure. Illustratively, Implant Innovations, Inc., of Palm Beach Gardens, Florida, has identified certain implant components by color, other components being undifferentiated by color. Still other parameters are also identified by color. Namely, angle of a prosthetic component is identified by color. Healing caps are identified by placing numbers on the top to indicate height and width of the abutment, and width of the corresponding implant. However, numerical designations are utilized for more than one parameter, which practice obviously can potentially be confusing. Furthermore, corresponding impression copings are not identified for compatibility in this scheme. It should be noted that both colors and numbers are utilized to indicate more than one type of characteristic. By contrast, in the present invention, colors are reserved for only one characteristic or parameter, and symbols such as numerals are reserved exclusively for another characteristic or parameter.

Other known schemes utilize color to identify width of the implant, but do not extend the identification scheme to components which are typically used in an implant procedure. Steri-Oss, of Yorba Linda, Calif., identifies implant width by color, with corresponding healing caps, and prosthetic components sharing the coloring scheme. Steri-Oss does not indicate height of components, by contrast with the present invention.

Lifecore Biomedical, of Chaska, Minn., identifies diameter of healing caps by letters, cuff height by numerals and flare diameter by a different set of numerals. Friatec of Irvine, Calif. indicates diameter of the implant by color.

Straumann Dental, of Waltham, Mass., utilizes color to identify implant diameters, one variety of abutment (a wide necked abutment), and implant insertion depth. Ace Surgical Supply Company, Inc., of Brockton, Mass., color codes self-tapping fixture mounts and etches implants and temporary healing caps with numbers to indicate implant head diameter. Paragon Implant Co., of Encino, Calif., identifies diameter of fixture mounts, impression copings, and restorative components by color. Healing caps are not included in the color coding scheme.

The prior art systems fail to identify all of the critical characteristics or parameters of healing caps and impression copings, which are handled by all dental practitioners who may participate in an implant procedure. These may include a surgical specialist who conducts the initial implantation of a permanent implant which will subsequently be utilized as a foundation to receive a permanent dental crown, and a restorative dentist, who places the crown on the implant. The prior art systems may also fail to assist support staff who must order, organize, sort, select, and perform other tasks with the many, small components of an extensive system of implant components.

As a consequence, many errors can arise from inability to perceive configurational characteristics of implant components. For example, it would be feasible for an impression coping of incorrect width to be used on any given implant in the absence of positive identification. This can lead to a mismatch of the restorative implant platform and the restoration. Restorations not fully occupying the platform will be less stable and more prone to accumulate dental plaque. In the opposite situation, wherein the restoration extends beyond the restorative platform, an inaccessible area below the restoration is created that is difficult if not impossible to clean adequately. Other consequences of mismatches include but are not necessarily limited to discomfort to the patient, poor esthetic results, and potential food impaction.

Inability to readily discriminate among implant components further impacts upon efficiency of a dental practice. Because the components are precisely machined, typically from titanium, they are quite expensive. Titanium has very good resistance to degradation in the environment of the human body, and because many components are utilized only temporarily over a period of months, components are often reusable. They may be cleaned, sterilized, and restored to inventory. In prior art systems, there exists a considerable potential for both dentists and dental auxiliary personnel to misidentify and mislabel implant components. Appropriate identification is laboriously accomplished given the small size of typical implant components. Identification of these components therefore imposes a significant burden in time on a dental practice, with attendant increased costs.

In current practice, a typical system may have as many as four nominal implant widths. Thus, a typical system may have at least thirty-six possible healing caps and twelve possible impression copings with the four basic varieties of implant. This calculation ignores, of course, possible variations in restorative abutments and abutment screws. Thus the total number of different individual components becomes quite great, and possible confusion increases correspondingly. There remains a need in the implant field for a comprehensive visual identification system which expedites immediate recognition of critical characteristics of implant components.

None of the aforementioned dental componentry, taken either singly or in combination, is seen to address the parameters of component identification addressed by the instant invention, or to describe the instant invention as claimed.

SUMMARY OF THE INVENTION

The present invention sets forth a comprehensive system for visually identifying healing caps and impression copings of an implant system. Color, indicia, and other visual elements are utilized so that associated components are quickly identified. The invention enables healing caps and impression copings to be clearly identified as to important structural characteristics such as critical dimensions to establish compatibility with respect to associated implants. In particular, the invention allows a practitioner to identify these characteristics by directly observing a healing cap even while the healing cap is in the patient's mouth.

The significant parameters by which healing caps must be identified include width of the restorative platform, height of the healing cap, and maximum diameter. Maximum diameter refers to the diameter of the healing cap taken where the healing cap flares or increases in diameter from its lowermost surface, which lowermost surface width corresponds to the width of the restorative platform. For impression copings, significant parameters are width of the associated restoration platform, and maximum diameter. Among these, the single most basic parameter is width of the restorative platform. Preferably, this characteristic is indicated by the most conspicuous form of marking, which is color. All components associated with any one width of restorative platforms display a single hue. Within those components associated with any one width, components are marked with indicia, engraved patterns, or surface texture to indicate a secondary parameter, such as maximum diameter. Indication of a third parameter, such as height, is indicated on healing caps in the form of marking or texturing different from those indicating the first and second parameters. In this way, indication of each parameter is clearly distinguished from indication of another parameter.

Illustratively, a component has a color or hue, a number, and a letter. The component is immediately categorized as belonging to one family of components compatible with a particular restoration platform width due to color. When the second parameter is identified as being associated with either the number or the letter, it is immediately apparent that the remaining alphanumeric character signifies the third parameter. It is not necessary to consult a guide, as may be required particularly for systems employing several numbers to identify different parameters, or where use of numbers or letters does not consistently indicate the same parameter throughout a set of implant components.

Accordingly, it is a principal object of the invention to enable healing caps and impression copings to be readily identified and categorized according to significant structural characteristics.

It is another object of the invention that identification be made by visual inspection.

It is a further object of the invention to provide that indication of the various parameters take different visual forms.

Still another object of the invention is that color indicate the most basic parameter.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
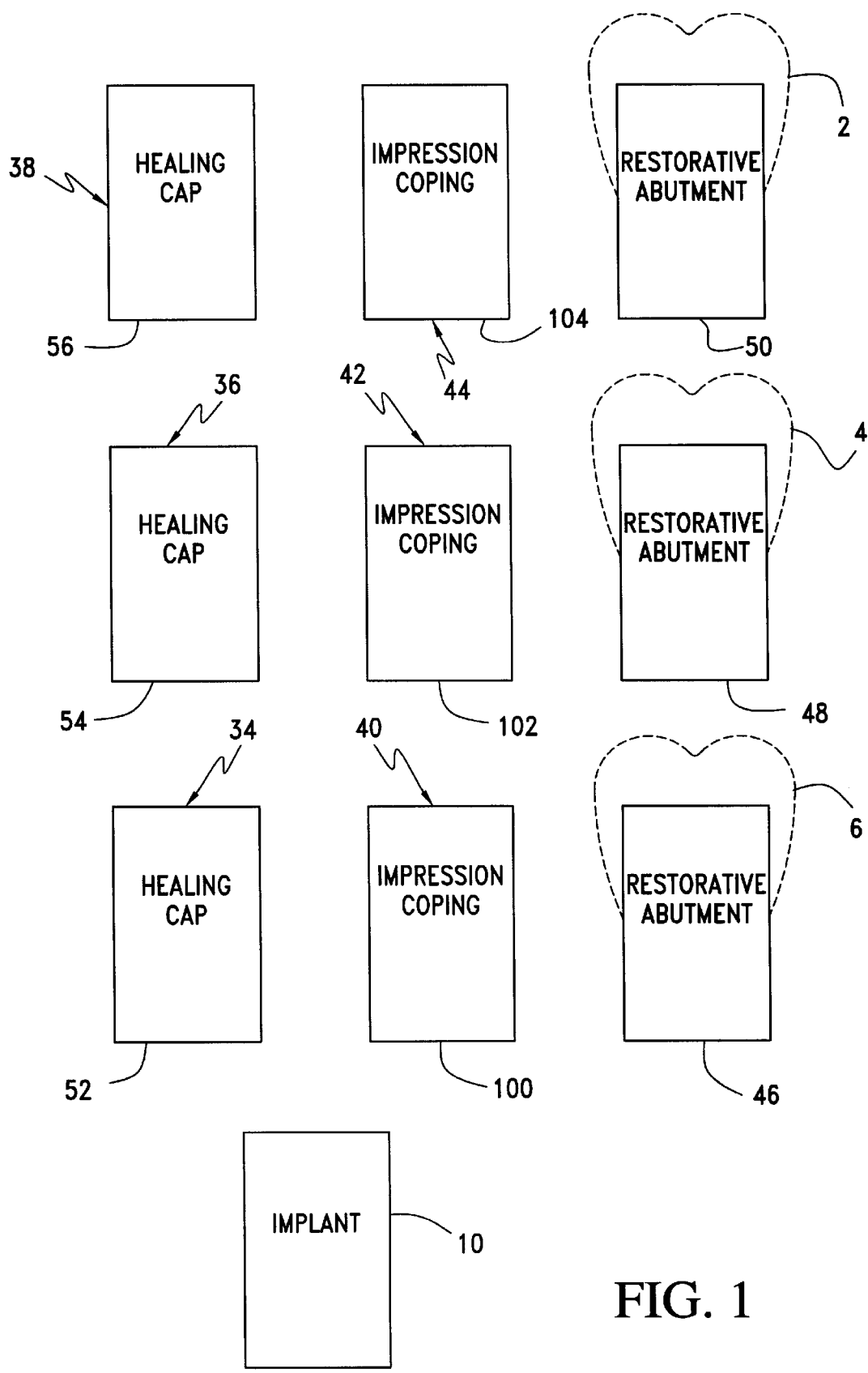
FIG. 1 is a diagrammatic representation of components of a system of dental implant components according to one embodiment of the invention, shown with restorations which may subsequently be utilized with some of the components.

FIG. 1 of the drawing shows components of a system of dental implant components which are available to a dental practitioner for use in an implantation procedure. The implant components and procedures are described herein for illustration only, and not in a limiting sense. In the illustrative example shown and described herein, the final goal is permanent implantation of a crown or restoration 2, 4, or 6 in the jaw of a patient (not shown). The procedure resulting in implantation of crown or restoration 2, 4, or 6 occurs in sequential stages, during which different components of the system come into play.

Figure 2:
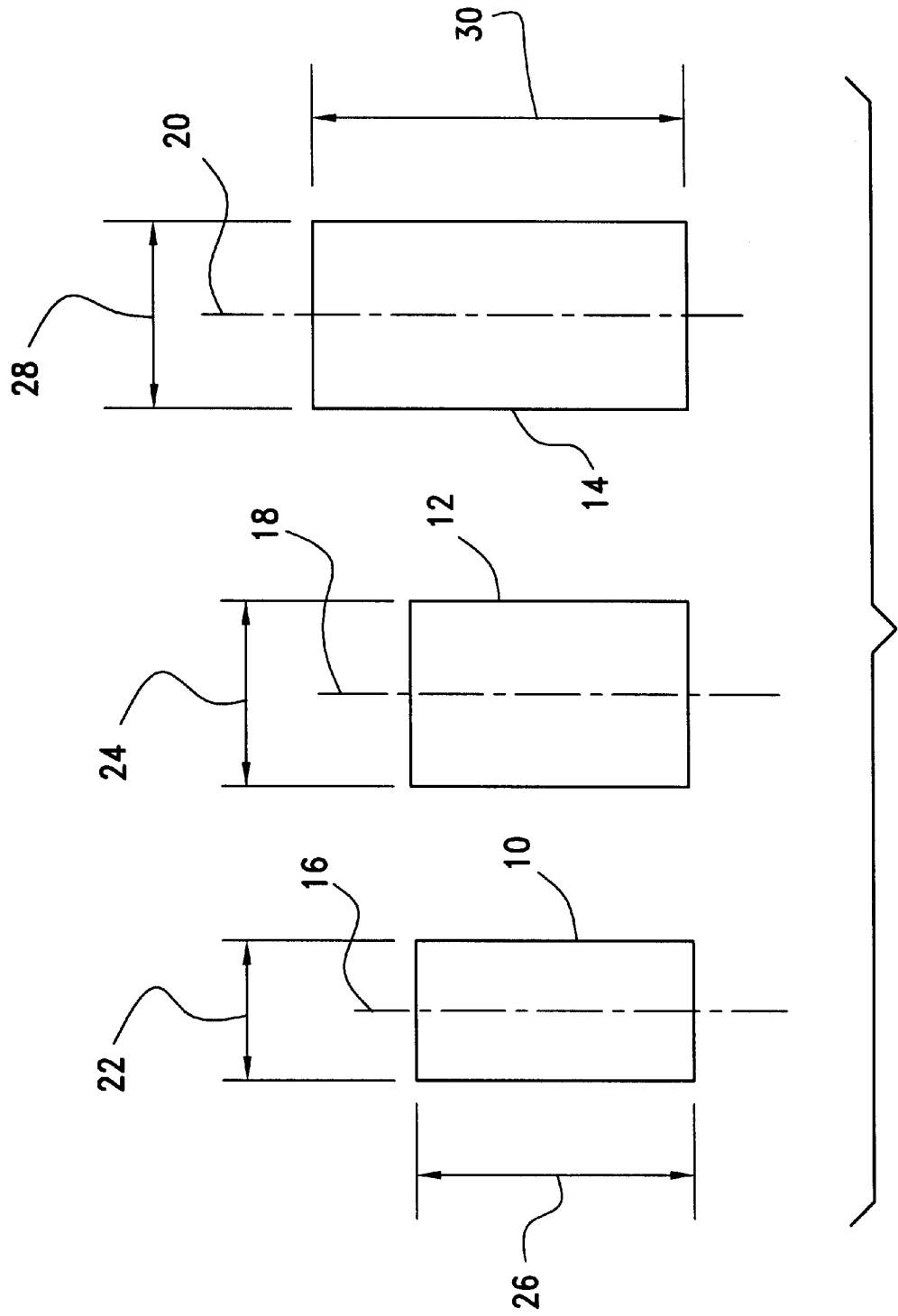
FIG. 2 is a diagrammatic representation of three implants which may be utilized with other components of the novel system, illustrating different dimensional characteristics.

Referring also to FIG. 2, the basic component is an implant 10, 12, or 14, which is osseointegrated into bone tissue of the jaw. Implants 10, 12, 14 have shanks (not shown) which are threaded or otherwise configured to engage bone tissue, and structure (not shown) for receiving and engaging a prosthesis. This structure is typically a hexagonal socket with or without threads to receive screws, but may vary from the described configuration. Implants 10, 12, 14 are of predetermined diameters or widths, and predetermined heights. FIG. 2 more particularly sets forth select dimensional characteristics and differences among implants 10, 12, 14. Height is the longitudinal dimension taken along respective axes 16, 18, 20, as depicted in FIG. 2, and corresponds to the vertical dimension when the implant 10, 12, or 14 is implanted in the jaw of a patient, and is viewed with the patient's head in a normal, upright orientation. In the example of FIG. 2, heights (indicated by arrows 26) of implants 10, 12 are equal in magnitude. However, diameters (indicated by arrows 22, 24) differ between implants 10, 12. Implant 14 has a diameter 28 equal in magnitude to diameter 24 of implant 12, but differs from implant 12 in that height 30 exceeds height 26 of implants 10, 12. As employed herein, diameter 22, 24, or 28 refers to the width of the upper surface or restorative platform of its respective implant 10, 12, or 14.

Returning to FIG. 1, it will be seen that a plurality of healing caps 34, 36, 38, a plurality of impression copings 40, 42, 44, and a plurality of subsequently fabricated restorative abutments 46, 48, 50 are or will become available for use with implant 10. Healing caps 34, 36, 38 share restorative platform widths (the widths at their lowermost surfaces) with that of implant 10, but differ in height. Likewise, impression copings 40, 42, 44 are of similar restorative platform width but differ in height. Finally, restorative abutments 46, 48, 50 are of similar restorative platform width but differ in height. Restorative abutments provide a structural platform for receiving and supporting crown or restoration 2, 4, or 6, shown in broken lines in FIG. 1. Restorative abutments, healing caps, and impression copings have structure for engaging and being retained by the implant. Typically, this structure includes a hexagonal post, but may alternatively include a hole for passing a screw that threads to the implant, or other structure. The healing caps, impression copings, restorative abutments, and implant shown for illustrative purposes in FIG. 1 are generally represented by generic blocks, and notably show only select dimensions and shape features of those typically employed in such componentry.

Width and height are selected by a dental practitioner for practical reasons, such as correct alignment of the prosthesis, strength and durability of the installation, and for esthetics. After implant 10 is implanted in the jaw, osseointegration occurs over several months. A temporary cover, provided by a healing cap 34, 36, or 38 is preferably installed in implant 10, and will later be removed when it is necessary to gain access to implant 10. Subsequently, one of impression copings 40, 42, 44 will be used. Finally, a suitable restorative abutment 46, 48, or 50 is installed on implant 10. Healing caps 34, 36, 38, impression copings 40, 42, 44, and restorative abutments 46, 48, 50 are all attachable implant components which utilize implant 10 as a foundation or base. It follows that in the example of FIG. 1, the family of implant components associated with implant 10 has a total count of some nine different components, in addition to implant 10. This number may be increased by additional nominal sizes of healing caps, impression copings, restorative abutments. For example, in current practice, healing abutments are provided in nominal heights of 2, 4, 6, and 8 millimeters. Preferably, the invention would encompass healing caps of at least four heights. The actual number depicted is representative, and is reduced from four only for purposes of simplifying explanation of the invention.

If implant 10 is not suitable due to its dimensions, then a different implant 12 or 14 must be selected to be the foundation or base for the final prosthetic installation. The issue of height also applies to healing caps. Each implant 10, 12, or 14 has in the present example three healing caps 34, 36, 38 and three impression copings 40, 42, 44 associated therewith although obviously these numbers, including the number and characteristics of implants, may be varied to suit. Implants 10, 12, 14 may be provided as part of a comprehensive system, or alternatively, a system of healing caps and impression copings may be provided as part of a system compatible with implants furnished by others. The system described herein thus includes thirty different components (at least three implants 10, 12, 14, and three each of healing caps 34, 36, 38, impression copings 40, 42, 44, and restorative abutments 46, 48, 50 for each implant), where classification is made according to structural differences among the various components. Of course, other systems could include additional variations with corresponding increase in the total count of components.

ROLE OF THE PRESENT INVENTION

The present invention provides a method of visually identifying and discriminating among these components. First, each implant 10, 12, or 14 has a nominal diameter or width of its restorative platform establishing a first category for healing caps and for impression copings. Illustratively, nominal industry dimensions of four, five, and six millimeters respectively result in a first category of healing caps compatible with a restorative platform width of four millimeters, a second category of healing caps compatible with restorative platform width of five millimeters, and a third category of healing caps compatible with restorative platform width of six millimeters. As employed in the field of dental implants, compatibility signifies that the attachable components share the nominal diameter dimension or restorative platform width of the base component, apart from negligible variations in manufacturing tolerances.

Figures 3, 4:
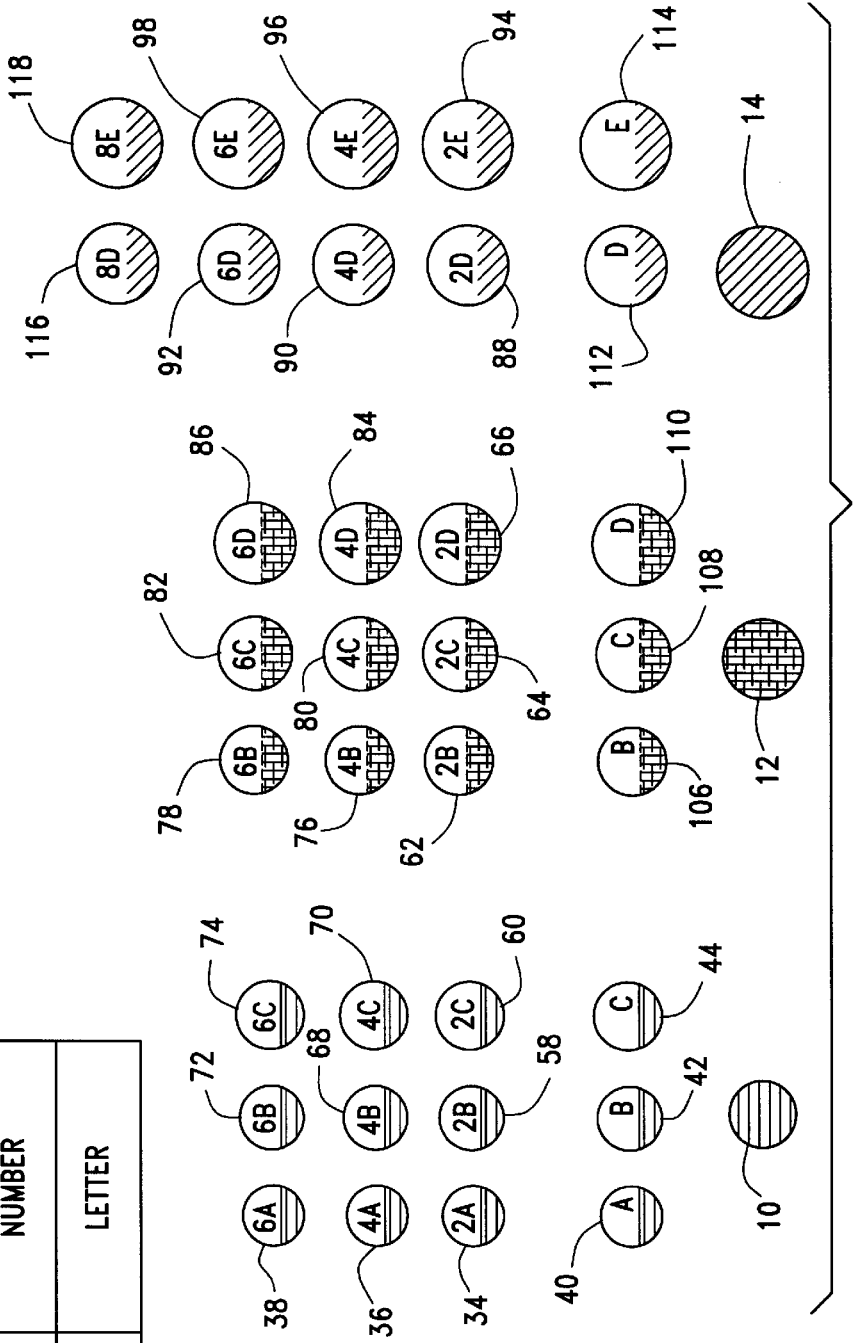
FIG. 3 is a diagrammatic top plan view of a system of components according to one embodiment of the present invention.
FIG. 4 is a table showing representative generic forms of visual indication of an exemplary classification scheme utilized to distinguish among the components of FIG. 3, and further shows characteristics indicated by each genus.

Illustration of a representative system of implant components including healing caps and impression copings is shown in FIG. 3. Components of the system are classified with respect to structural characteristics thereof. In most cases, the structural characteristics are dimensional, but as discussed hereinafter, could be configurational. The system includes at a minimum healing caps and impression copings, but may encompass implants and still other components such as restorative abutments (see FIG. 1).

Each implant 10, 12, or 14 is preferably provided with one species of a first generic form of visual indication at a visible location thereon. In the preferred embodiment, color or hue indicates width or diameter of the restorative platform. A selection of hues constitutes the first generic form of visual indication, with each individual or unique hue being one species of the selection of hues.

Healing caps, impression copings, and restorative abutments are classified firstly according to compatibility with implants, and secondarily according to other characteristics. Healing caps are classified according to three parameters.

The first parameter, which is the most fundamental when sorting implant components, is compatibility with the implant. This requires that each healing cap have a lower surface 52, 54, or 56, representatively shown in FIG. 1 for respective healing caps 34, 36, 38. It will be understood that the lower surface is that which abuts the uppermost surface or restorative platform of the associated implant, and does not encompass surfaces of a threaded or polygonal shank provided for secure engagement of the implant. Each healing cap is classified in one of at least two width categories, wherein a first width category corresponds to a first nominal width of restorative platforms of implants, and a second width category corresponds to a second nominal width of restorative platforms of implants.

This is illustrated in FIG. 3, wherein healing caps 34, 36, 38, 58, 60, 68, 70, 72, 74, which are similar to one another with respect to width category, taken at the lower surface of each, are compatible with implant 10. Alternatively stated, healing caps 34, 36, 38, 58, 60, 68, 70, 72, 74, are members of one width category, where that category signifies compatibility with the restorative platform of implant 10.

Similarity in this fundamental characteristic is preferably indicated by the most conspicuous or readily perceived visual characteristic, which is that of color or hue. In FIG. 3, implant 10 and every component attachable thereto have at least a patch of blue color. Indication of width of the restorative platform of implant 10 by coloring implant 10 is shown in FIG. 3 although this is optional. The color may cover the entire surface or any visually significant portion thereof, either continuously or discontinuously. It is noted that for purposes of illustration, variations in color or hue are represented by variations in hatching and the like in the elements of FIG. 3.

Thus it is seen that every healing cap, impression coping, and other attachable component which is compatible with implant 10 is immediately differentiated from other healing caps, impression copings, and other attachable components which would not be suitable for use with implant 10. Immediate recognition as to which size of implant is used is highly desirable, since most dental practitioners and assistants will typically be selecting components for use with an installed implant. Even when components are being cleaned and sterilized for subsequent reuse, classification according to compatibility with a particular implant nominal diameter or width is desirable. The components may then be efficiently selected and otherwise handled by dental personnel.

Implant 12 and healing caps 62, 64, 66, 76, 78, 80, 82, 84, 86, which are compatible with implant 12, have gold coloring. Implant 14 and healing caps 88, 90, 92, 94, 96, 98, which are compatible with implant 14, have green coloring.

A second parameter important in categorizing healing caps is that of height. Height of each healing cap is indicated by a species of a second generic form of visual identification. In the example of FIG. 3, height is indicated by an Arabic numeral, or number. This number may correspond to height in millimeters, although another numbering convention may be adopted if desired. Regardless of the convention selected, it is immediately seen due to the benefits afforded by the inventive system and method of identification that healing caps 34, 58, 60, 62, 64, 66, 88, 94 are of similar height despite differences in other characteristics. In a similar vein, healing caps 34, 36, 38 differ in height even though being identical with respect to compatibility with implant 10 and with maximum diameter of the respective healing cap. Similarly, healing caps 116, 118 differ in height from healing caps 88, 90, 92, 94, 96, 98. Healing caps, 116, 118 are part of a family of components compatible with implant 14, wherein healing caps are available in heights of two, four, six, and eight millimeters, as indicated by numerals.

The third parameter of healing caps which is desirable to indicate is that of maximum diameter thereof. Members of each maximum diameter category are indicated by a letter of the Roman alphabet in the example of FIG. 3. The table of FIG. 4 may be consulted to determine which characteristics are indicated by which forms of visual identification in the example of FIG. 3. Preferably, and as illustrated in FIG. 3, indications of all three parameters are located on and are simultaneously visible from a single side of any implant component bearing such indications. A dental practitioner can therefore take in at a glance the nature of any one component without having to inspect different sides of that component. It will be appreciated that the families of components associated with implants 10, 12, and 14 are not readily differentiated by examining FIG. 3. This emphasizes the problem of visual identification of actual components being addressed by the present invention. It is noted that the visible variations in diameters seen in FIG. 3, such as those between healing caps 34, 58, and 60, generally correspond to differences in maximum diameters. The dimensional differences in restorative widths and in heights are not readily apparent from the view shown in FIG. 3, except as advantageously achieved by the inventive system and method of identification provided by the instant invention. Actual differences are depicted in exaggerated manner in FIG. 5, which illustrates some of the components seen in top plan view in FIG. 3.

Figure 5:
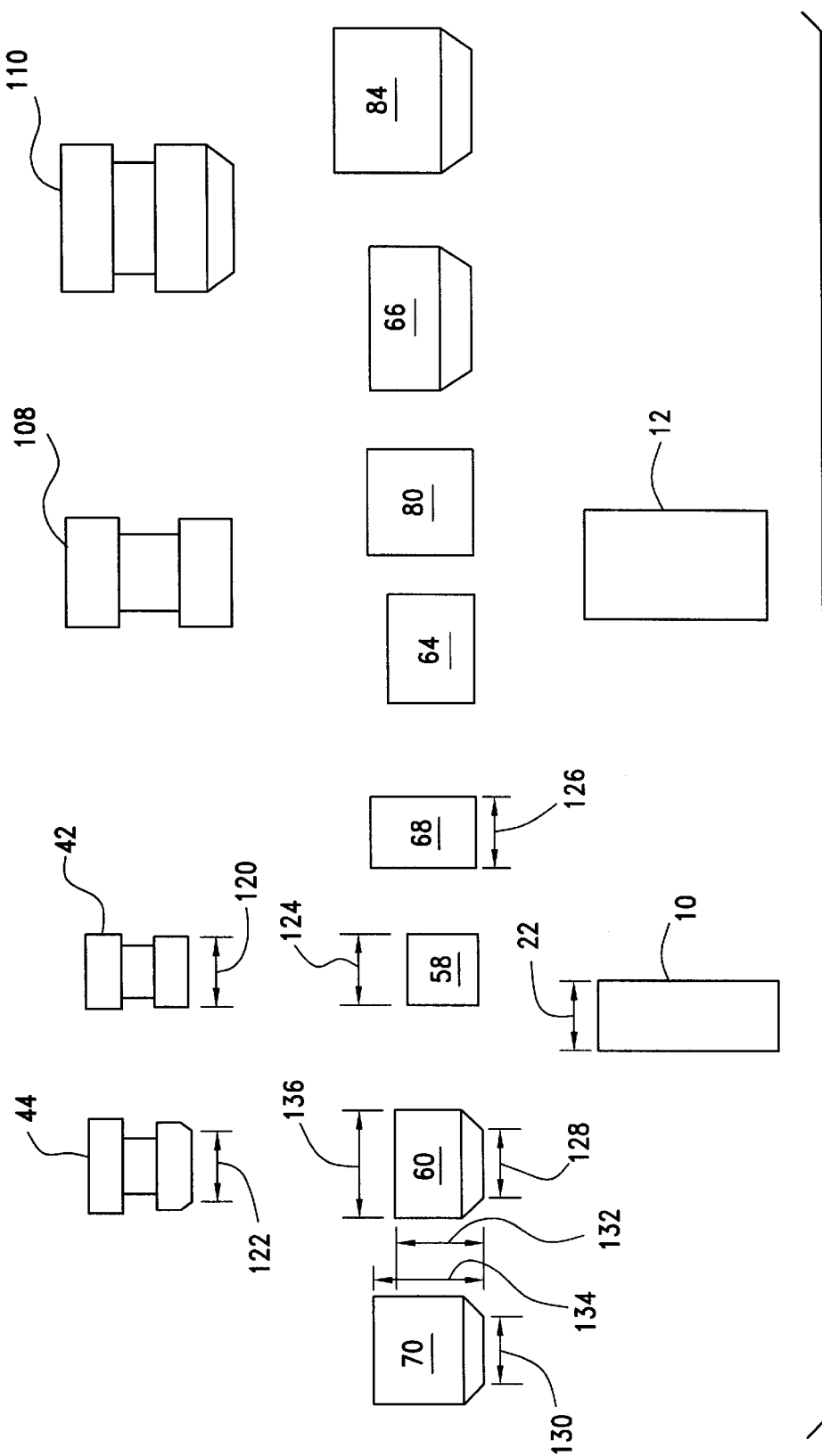
FIG. 5 is a side elevational detail view showing some of the components of FIG. 3, shown in enlarged scale.

In FIG. 5, impression copings 42, 44 are compatible with implant 10 due to similarity of their respective widths or diameters 120, 122 with width or diameter 22 of implant 10. Healing caps 58, 68 are compatible with implant 10 due to similarity of respective maximum diameters 124, 126, and differ from one another in height. Healing caps 60, 70 are compatible with implant 10 due to similarity of respective widths or diameters 128, 130. Healing caps 60, 70 differ from one another in that they have different heights, as indicated by respective arrows 132, 134. Healing caps 58, 68 differ from healing caps 60, 70 in that the former have a maximum diameter 124 (shown for healing cap 58, but applying equally to healing cap 68), whereas the latter have a maximum diameter 136 (shown only for healing cap 60, but applying equally to healing cap 70) which is greater in magnitude than diameter 124. Similar differences occur in the family including implant 12, healing caps 64, 66, 80, 84, and impression copings 108, 110, although specific dimensions are not called out herein.

It will be appreciated that each hue is one species of a first generic form of visual indication including a selection of hues. Similarly, each number is one species of a second generic form of visual indication encompassing Arabic numerals, and each letter is one species of a third generic form of visual indication encompassing letters of the Roman alphabet. Different individual species selected from the respective generic group are utilized to indicate each distinguishable dimension or characteristic being indicated by the genus. In the example of FIG. 3, the second and third generic forms of visual indication respectively include indicia characters of a first related group of indicia characters and indicia characters of a second related group of indicia characters. As employed herein, relation signifies membership in a well known group of associated symbols. Other related groups of indicia characters could include, illustratively, other alphabets, such as Greek, Cyrillic, and others; astrological signs, mathematical or scientific symbols and characters, geometric shapes, and still others.

Impression copings are placed into at least two categories. As in the case of healing caps, impression copings are first classified according to magnitude of the width taken at the lower surface of each impression coping, such as surfaces 100, 102, 104 (see FIG. 1). As in the case of healing caps, the lower surface of impression copings is that surface abutting and corresponding to the restorative platform of the associated implant. Categories corresponding to width of the compatible restorative platform are indicated by color, utilizing the same indication convention as that utilized to indicate healing caps. Illustratively, impression copings 40, 42, 44 are compatible with implant 10, and differ according to their maximum diameter. The latter characteristic is indicated by letters. Impression copings 106, 108, 110 are compatible with implant 12, and differ according to maximum diameter. Impression copings 112, 114 are compatible with implant 12, and differ according to maximum diameter. The maximum diameters of impression copings 44, 108 are similar, and the maximum diameters of impression copings 110, 112 are similar.

Coloring or hue is applied in any suitable manner, such as staining, anodizing, heating, metal plating, chemical treatment, or in any other way. Indicia characters may be applied by laser etching microengraving or in any other suitable way. Any method which results in indicia being visually perceptible would be acceptable.

It is an important feature of the invention that similar indication conventions apply to each characteristic which is indicated thereby. Therefore, compatibility with implants of all attachable components of the implant system, including at least healing caps and impression copings, and preferably all associated other components such as, for example, restorative abutments, is indicated by the same scheme of coloring as that by which implants of different restoration platforms are differentiated. Similarly, where component height is indicated, the same convention of numbers or other selected genus of visual identification is employed. Where maximum component diameter is indicated, letters or other selected genus of visual identification is employed. These schemes are similar as regards individual species as well as genus. Thus, consistency aids in intuitive mastering of visual indication of classification.

The invention may be regarded both as a method of identifying components of a system of dental implant components, and also as a classified collection or system of dental implant components for an implantation procedure wherein a prosthesis is to be mounted to an implant which is to be osseointegrated in bone tissue of a patient. Where regarded as the method, the steps include classifying components as described above, providing visual indication at a visible location on each component as to which category it is a member, wherein visual indication includes selection of genuses and species within each genus, as described above.

The novel method may extended to include additional classifications. An illustrative further classification could be based on the purpose of the components. In another optional illustration, restorative abutments could be classified according to the invention. Implants and associated attachable components could be categorized by styles of mutual engagement structure.

Components of the system are classified and visually marked, with certain exceptions. One exception is that components which by virtue of their external configuration are so distinctive or which occur in only one form such that no intentional indication of their nature is necessary to differentiate such components from others may be ignored for the purposes of classifying and indicating. A possible example is that of abutment fastening screws. A second exception is that the native color of one category of components may be left unchanged by not intentionally introducing coloring. In this case, the native color would be regarded as a provided color as long as differentiation is provided by suitably coloring other components. As an example, because most implant components are fabricated from titanium, the dull gray silver color characteristic of titanium may be regarded as being a provided hue.

The concept of leaving components unmarked or left devoid of visual indications may be practiced to provide a recognizable category. For example, a component lacking an alphabetical or numerical character, where other components of a related family of components have a character, could be understood to be indicative of a specific designated characteristic. The most frequently used characteristics could, under this embodiment of the invention, be identified by lack of indicia characters or in other ways. Inclusion of lack of intentionally introduced visual indication has the advantage of reducing requirements of undertaking steps to mark components, thereby reducing costs.

The novel method of identification may be expanded to encompass additional parameters. Different external configurations of otherwise similar components may be indicated. Alternatively, the method may be modified to delete one or more of the illustrative parameters described herein, and to encompass other parameters thereinstead.

Dimensions other than nominal sizes may be signalled by the novel method. For example, variations generally within a nominal size may be the subject of additional or different forms of visual indication. It may, for example, be desired to provide intermediate sizes or variations within a single nominal size.

It is to be understood that the present invention is not limited to the embodiments described above, but encompasses any and all embodiments within the scope of the following claims.

I claim:

1. A method of identifying components of a system of dental implant components used in an implantation procedure with respect to structural characteristics of the components, wherein each implant usable with the system of implant components has a restorative platform having width, said method comprising the steps of:

classifying healing caps of the system according to magnitude of the width taken at the lower surface of each healing cap, which lower surface is to abut the implant, where the width taken at the lower surface corresponds to the width of the restorative platform of one implant usable with the system, such that each healing cap is classified in one of at least two width categories including a first width category corresponding to a first nominal width of restorative platforms of implants and a second width category corresponding to a second nominal width of restorative platforms of implants;

providing a first species of a first generic form of visual indication at a visible location on each healing cap which is a member of the first width category;

providing a second species of the first generic form of visual indication at a visible location on each healing cap which is a member of the second width category;

classifying healing caps of the system according to magnitude of the height of each healing cap such that each healing cap is classified in one of at least two height categories including a first height category and a second height category;

providing a first species of a second generic form of visual indication at a visible location on each healing cap which is a member of the first height category;

providing a second species of the second generic form of visual indication at a visible location on each healing cap which is a member of the second height category;

classifying healing caps of the system according to maximum diameter of each healing cap such that each healing cap is classified in one of at least two maximum diameter categories including a first maximum diameter category and a second maximum diameter category;

providing a first species of a third generic form of visual indication at a visible location on each healing cap which is a member of the first maximum diameter category;

providing a second species of the third generic form of visual indication at a visible location on each healing cap which is a member of the second maximum diameter category;

classifying impression copings of the system of components according to magnitude of the width taken at the lower surface of each impression coping, where the width taken at the lower surface corresponds to the width of the restorative platform of one implant usable with the system, such that each impression coping is classified in one of at least two width categories including a first width category corresponding to a first nominal width of restorative platforms of implants and a second width category corresponding to a second nominal width of restorative platforms of implants;

providing the first species of the first generic form of visual indication at a visible location on each impression coping which is a member of the first width category; and providing the second species of the first generic form of visual indication at a visible location on each impression coping which is a member of the second width category.

2. The method of identifying components of a system of dental implant components according to claim 1, comprising the further step of:

classifying impression copings of the system of components according to maximum diameter of each impression coping, such that each impression coping is classified in one of at least two maximum diameter categories including a first maximum diameter category and a second maximum diameter category;

providing visual indication at a visible location on each impression coping which is a member of the first maximum diameter category; and providing visual indication at a visible location on each impression coping which is a member of the second maximum diameter category, wherein the visual indication of the first maximum diameter category is visibly distinguishable from that of the second maximum diameter category.

3. The method of identifying components of a system of dental components according to claim 2, comprising the further step of locating all visual indications of each healing cap on one side of each respective healing cap and all visual indications of each impression coping on one side of each respective impression coping such that the visual indications of all parameters are simultaneously visible from a single side of any implant component bearing such indications.

4. The method of identifying components of a system of dental implant components according to claim 2, wherein said step of providing visual indication at a visible location on each impression coping which is a member of the first maximum diameter category, and said step of providing visual indication at a visible location on each impression coping which is a member of the second maximum diameter category each comprise the further step of utilizing the same indication convention as that utilized to indicate maximum diameter of healing caps.

5. The method of identifying components of a system of dental implant components according to claim 1, wherein said step of providing a first species of a first generic form of visual indication at a visible location on each healing cap which is a member of the first width category comprises the further step of providing a first hue of a selection of hues, said step of providing a second species of the first generic form of visual indication at a visible location on each healing cap which is a member of the second width category comprises the further step of providing a second hue of the selection of hues, said step of providing the first species of the first generic form of visual indication at a visible location on each impression coping which is a member of the first width category comprises the further step of providing the first hue of the selection of hues; and said step of providing the second species of the first generic form of visual indication at a visible location on each impression coping which is a member of the second width category comprises the further step of providing the second hue of the selection of hues.

6. The method of identifying components of a system of dental implant components according to claim 1, wherein said step of providing a first species of a second generic form of visual indication comprises the further step of providing one indicia character of a first related group of indicia characters, and wherein said step of providing a second species of a second generic form of visual indication comprises the further step of providing a different indicia character of the first related group of indicia characters.

7. The method of identifying components of a system of dental implant components according to claim 6, including the further step of selecting the first related group of indicia characters from one set of the set of the Roman alphabet and the set of Arabic numerals.

8. The method of identifying components of a system of dental implant components according to claim 6, wherein said step of providing a first species of a third generic form of visual indication comprises the further step of providing one indicia character of a second related group of indicia characters different from those of the first related group, and said step of providing a second species of a third generic form of visual indication comprises the further step of providing a different indicia character of the second related group of indicia characters.

9. The method of identifying components of a system of dental implant components according to claim 8, including the further steps of selecting the first related group of indicia characters from one set of the set of the Roman alphabet and the set of Arabic numerals, and selecting the second related group of indicia characters from the other set of the set of the Roman alphabet and the set of Arabic numerals.

10. The method of identifying components of a system of dental implants according to claim 1, including the further steps of classifying implants of the system according to magnitude of the widths of the restorative platforms of implants usable with the system, such that each implant is classified in one of the width categories;

providing the first species of the first generic form of visual indication at a visible location on each implant which is a member of the first width category; and providing the second species of the first generic form of visual indication at a visible location on each implant cap which is a member of the second width category.

11. A system of dental implant components for an implantation procedure wherein a prosthesis is to be mounted to an implant which is to be osseointegrated in bone tissue of a patient, comprising:

a plurality of healing caps each having a lower surface, height, and a maximum diameter, wherein at least two of said healing caps differ in width at said lower surface of each, at least two of said healing caps differ in height, at least two of said healing caps differ in maximum diameter, and each of said healing caps is provided with one species of a first generic form of visual indication visibly located thereon, wherein each said species of said first generic form of visual indication indicates one magnitude of width at said lower surface of its associated said healing cap, each of said healing caps is provided with one species of a second generic form of visual indication visibly located thereon, wherein each said species of said second generic form of visual indication indicates one magnitude of height of its associated said healing cap, and each of said healing caps is provided with one species of a third generic form of visual indication visibly located thereon, wherein each said species of said third generic form of visual indication indicates one magnitude of maximum diameter of its associated said healing cap; and a plurality of impression copings each having a lower surface and a maximum diameter, wherein at least two of said impression copings differ in width at said lower surface of each and at least two of said impression copings differ in maximum diameter, and each of said impression copings is provided with one species of said first generic form of visual indication visibly located thereon, wherein each said;species of said first generic form of visual indication indicates one magnitude of width at said lower surface of its associated said impression coping, and each of said impression copings is provided with one species of said third generic form of visual indication visibly located thereon, wherein each said species of said third generic form of visual indication indicates one magnitude of maximum diameter of its associated said healing cap, and said species of said first generic form of visual indication and said species of said third generic form of visual indication utilize the same indication convention to indicate similar structural characteristics of both said healing caps and said impression copings.

12. The system of dental implant components for an implantation procedure according to claim 11, wherein said first generic form of visual indication is a selection of hues, and each species of said first generic form of indication is a unique hue.

13. The system of dental implant components for an implantation procedure according to claim 11, wherein said second generic form of visual indication comprises a first related group of indicia characters wherein each species of said second generic form of visual indication is one indicia character of said first related group of indicia characters, and wherein said third generic form of visual indication comprises a second related group of indicia characters wherein each species of said second generic form of visual indication is one indicia character of said second related group of indicia characters.

14. The system of dental implant components for an implantation procedure according to claim 11, wherein said plurality of healing caps includes at least one healing cap having height of two millimeters, at least one healing cap having height of four millimeters, at least one healing cap having height of six millimeters, and at least one healing cap having height of eight millimeters.

15. The system of dental implant components for an implantation procedure according to claim 11, further including a plurality of implants including at least one implant having a restorative platform of a first width and at least one implant having a restorative platform of a second width, wherein said first width corresponds in magnitude to width of a first healing cap of said plurality of healing caps, and said second width corresponds in magnitude to width of a second healing cap of said plurality of healing caps, wherein said first healing cap differs in width from said second healing cap.

16. The system of dental implant components for an implantation procedure according to claim 11, wherein said first generic form of visual identification, said second generic form of visual identification, and said third generic form of visual identification are all located on one side of each dental implant component bearing said first generic form of visual identification, said second generic form of visual identification, and said third generic form of visual identification, whereby visual indications of all parameters are simultaneously visible from a single side of any implant component bearing such indications.

* * * * *